United States Patent
Gome

(10) Patent No.: US 7,960,586 B2
(45) Date of Patent: Jun. 14, 2011

(54) PURIFICATION OF ARMODAFINIL

(75) Inventor: Boaz Gome, Rishon-Lezion (IL)

(73) Assignee: Teva Pharmaceutical Industries Ltd., Petah Tiqva (IL)

( * ) Notice: Subject to any disclaimer, the term of this patent is extended or adjusted under 35 U.S.C. 154(b) by 332 days.

(21) Appl. No.: 12/229,048

(22) Filed: Aug. 18, 2008

(65) Prior Publication Data

US 2009/0048464 A1 Feb. 19, 2009

Related U.S. Application Data

(60) Provisional application No. 60/956,269, filed on Aug. 16, 2007, provisional application No. 60/971,351, filed on Sep. 11, 2007, provisional application No. 61/127,408, filed on May 12, 2008.

(51) Int. Cl.
*C07C 233/05* (2006.01)
(52) U.S. Cl. .................................................. 564/162
(58) Field of Classification Search ............... 564/162
See application file for complete search history.

(56) References Cited

U.S. PATENT DOCUMENTS

| | | | |
|---|---|---|---|
| 4,177,290 A | 12/1979 | Lafon | |
| 4,927,855 A | 5/1990 | Lafon | |
| 6,649,796 B2 | 11/2003 | Naddaka et al. | |
| 6,875,893 B2 | 4/2005 | Largeau et al. | |
| 7,057,068 B2 | 6/2006 | Castaldi et al. | |
| 7,057,069 B2 | 6/2006 | Largeau et al. | |
| 2002/0043207 A1 | 4/2002 | Singer et al. | |
| 2005/0080256 A1 | 4/2005 | Rebiere et al. | |
| 2005/0154063 A1 | 7/2005 | Castaldi et al. | |
| 2005/0282821 A1 | 12/2005 | Lesur et al. | |
| 2006/0086667 A1* | 4/2006 | Hauck et al. | 210/656 |
| 2006/0128812 A1 | 6/2006 | Bhatt et al. | |
| 2006/0135621 A1 | 6/2006 | Neckebrock et al. | |
| 2006/0160903 A1 | 7/2006 | Liang | |
| 2007/0015836 A1 | 1/2007 | Rose | |
| 2009/0281193 A1* | 11/2009 | Neckebrock et al. | 514/618 |
| 2010/0210731 A1* | 8/2010 | Hickey et al. | 514/618 |

FOREIGN PATENT DOCUMENTS

| | | |
|---|---|---|
| WO | WO 2004/060858 | 7/2004 |
| WO | WO 2005/000799 | 1/2005 |
| WO | WO 2005/023198 | 3/2005 |
| WO | WO 2005/028428 | 3/2005 |
| WO | WO 2005/042479 | 5/2005 |
| WO | WO 2005/077894 | 8/2005 |
| WO | WO 2006/030278 | 3/2006 |
| WO | WO 2007/103221 | 9/2007 |

OTHER PUBLICATIONS

Osorio-Lozada, et al., "Synthesis and determination of the absolute stereochemistry of the enantiomers of adrafinil and modafinil", Tetrahedron: Asymmetry 15 (2004) 3811-3815.
ICH Good Manufacturing Practice Guide for Active Pharmaceutical Ingredients, Q7A, Current Step 4 Version (Nov. 10, 2000), pp. 1-43.
Pharmacopeial Forum, vol. 24, No. 1, pp. 5438-5440 (Jan.-Feb. 1998).
Li et al., "Relationship Between Physical Properties and Crystal Structures of Chiral Drugs," J. Pharmaceutical Sciences, 86(10), 1073-1078 (1997).
Anonymous, "Recrystallization", Wikipedia, The Free Encyclopedia [online], Dec. 2007, retrieved from the Internet: URL:http://en.wikipedia.org/wiki/Recrystallization.
Prisinzano, et al., "Synthesis and Determination of the Absolute Configuration of the Enantiomers of Modafinil", Tetrahedron: Asymmetry, vol. 15 (2004) 1053-1058.
Oae, "Organic Chemistry of Sulfur" Plenum Press N.Y. 1977, p. 383-471.
Office Action from related U.S. Appl. No. 11/709,906, mailed Feb. 13, 2008.

* cited by examiner

*Primary Examiner* — Shailendra Kumar
(74) *Attorney, Agent, or Firm* — Kenyon & Kenyon LLP

(57) ABSTRACT

The invention encompasses processes for obtaining pure armodafinil substantially free of disulfide impurities that is suitable for use on an industrial scale. In particular, a processes for purifying armodafinil from bis(diphenylmethyl) disulfide comprising: dissolving crude armodafinil in ethanol to form a solution; adding a solvent selected from the group consisting of linear or branched $C_5$-$C_8$ alkyl, linear or branched $C_5$-$C_8$ ether, and mixtures thereof to the solution to form a reaction mixture; cooling the reaction mixture; and isolating pure armodafinil from the reaction mixture.

23 Claims, No Drawings

PURIFICATION OF ARMODAFINIL

CROSS-REFERENCE TO RELATED APPLICATIONS

This application claims the benefit of U.S. provisional application Ser. Nos. 60/956,269, filed Aug. 16, 2007; 61/127,408, filed May 12, 2008; and 60/971,352, filed Sep. 11, 2007, hereby incorporated by reference.

FIELD OF THE INVENTION

The invention encompasses processes for obtaining pure armodafinil substantially free of disulfide impurities that is suitable for use on an industrial scale.

BACKGROUND OF THE INVENTION

Modafinil ("MDF") is currently marketed by Cephalon, Inc. under the trade name PROVIGIL® as a racemic mixture of its R and S enantiomers. PROVIGIL® is used for the treatment of excessive sleepiness associated with narcolepsy, shift work sleep disorder ("SWSD"), and obstructive sleep apnea/hypopnea syndrome ("OSA/HS").

Studies have shown that while both enantiomers of modafinil are pharmacologically active, the S enantiomer is eliminated from the body three times faster than the R enantiomer. Prisinzano et al., *Tetrahedron: Asymmetry*, vol. 5 (2004) 1053-1058. It is, therefore, preferable to develop pharmaceutical compositions of the R enantiomer of modafinil, as opposed to its racemic mixture.

The R enantiomer of modafinil is known as armodafinil and has the chemical name (−)-2-[(R)-(diphenylmethyl)sulfinyl]acetamide. The molecular weight of armodafinil is 273.35 and it has the following chemical structure:

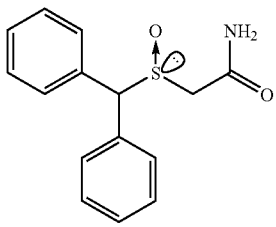

Armodafinil is commercially available as NUVIGIL™. Armodafinil is well tolerated and has the safety profile comparable to modafinil.

Armodafinil was first disclosed in the U.S. Pat. No. 4,927,855 ("the '855 patent") and in EP Publication No. 0233106, both of which are assigned to Lafon Laboratories.

The preparation of armodafinil is also disclosed in the '855 patent and it is summarized in the following scheme:

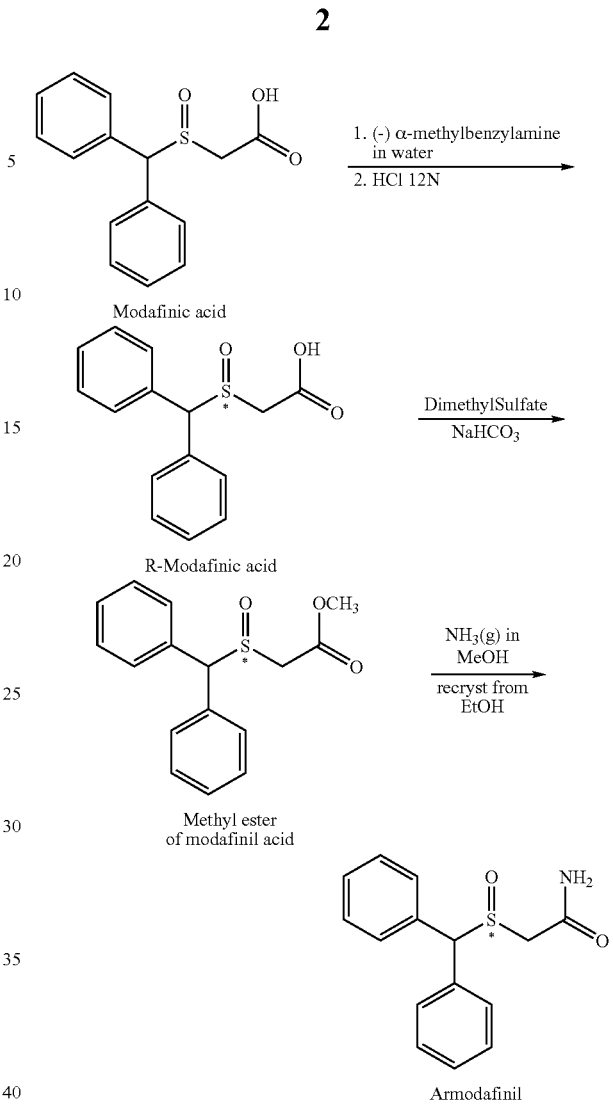

See '855 patent, col. 2, 11. 16-53.

The process disclosed in the '855 patent uses (−)-α-methylbenzylamine in the resolution step. Furthermore, two additional crystallization steps are performed in order to increase the enantiomeric purity of the modafinic acid. As a consequence, the overall yield of 32% reported in the '855 patent is rather unsatisfactory for large scale commercial use.

During the preparation of armodafinil, an impurity, bis (diphenylmethyl)disulfide ("R-MDF-DS") may be formed. R-MDF-DS has the following structure:

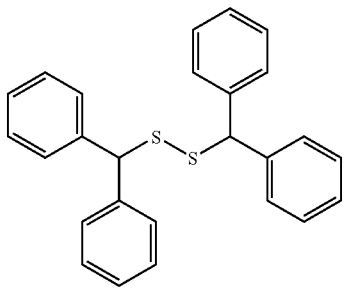

$C_{26}H_{22}S_2$
Mol. Wt.: 398.58

PCT Publication No. WO 2007/103221 describes a process for the preparation of bis(diphenylmethyl)disulfide ("R-MDF-DS") and a process for reducing the amount of R-MDF-DS in armodafinil comprising suspending armodafinil in $C_5$ to $Cl_2$ hydrocarbon. PCT Publication No. WO2007/103221 relates, among other aspects, to armodafinil containing less than about 0.2% area by HPLC of bis (diphenylmethyl) disulfide.

Oae, S., "The Organic Chemistry of Sulfur", Plenum Press, N.Y., 1977, describes the following mechanism for obtaining bis(diphenylmethyl)disulfide, wherein RSH in this case is unstable leading to the disulfide, RSSR, wherein R is alkyl or aryl.

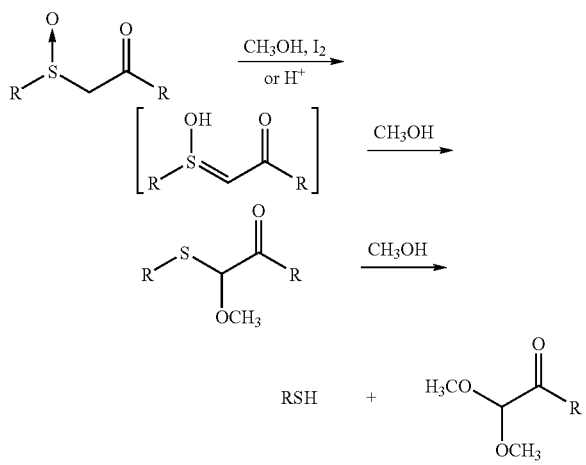

Given the low yields and disulfide impurities present in the processes of the prior art, there is a need in the art for improved processes for obtaining optically and chemically pure armodafinil substantially free of disulfide impurities that will be suitable for industrial scale synthesis.

SUMMARY OF THE INVENTION

In one embodiment, the present invention encompasses a process for purifying armodafinil from R-MDF-DS comprising: dissolving crude armodafinil in ethanol to form a solution; adding a solvent selected from the group consisting of linear or branched $C_5$-$C_8$ alkyl, linear or branched $C_5$-$C_8$ ether, and mixtures thereof to the solution to form a reaction mixture; cooling the reaction mixture; and isolating pure armodafinil from the reaction mixture.

In another embodiment, the present invention encompasses a process for preventing the transformation of armodafinil to S-modafinil comprising: dissolving crude armodafinil in at least about 15 ml of ethanol per gram of crude armodafinil to form a solution; adding activated basic or neutral $Al_2O_3$ to the solution to form a reaction mixture; and isolating the purified armodafinil from the reaction mixture.

Yet another embodiment encompasses a process for purifying armodafinil comprising dissolving crude armodafinil in at least about 15 ml of ethanol per gram of crude armodafinil to a form a solution; adding activated basic alumina or neutral alumina to the solution to form a reaction mixture; and isolating the purified armodafinil from the reaction mixture.

DETAILED DESCRIPTION OF THE INVENTION

The present invention encompasses processes for obtaining pure armodafinil substantially free of disulfide impurities that is suitable for use on an industrial scale.

As used herein, the term "activated alumina" refers activated basic alumina or neutral alumina unless otherwise defined to refer to a particular type of alumina.

As used herein, the term "quantization limit" or "QL" when referring to R-MDF-DS refers to the lowest level of impurity in which the concentration can be determined which typically refers to less than about 0.05% area as measured by high performance liquid chromatography ("HPLC").

As used herein, the term "crude armodafinil" refers to armodafinil containing more than about 0.4% area of R-MDF-DS impurities as measured by high performance liquid chromatography ("HPLC"), preferably more than about 0.5% area of R-MDF-DS impurities, more preferably, more than about 0.8% area, more preferably 1% area, more preferably 1.2%, and most preferably more than about 1.5% area as measured by HPLC.

As used herein, the term "pure armodafinil" refers to armodafinil containing less than about 0.15% area of R-MDF-DS impurities, as measured by HPLC, preferably less than about 0.10%, more preferably less than about 0.05%, and/or less than about 0.05% area of S-modafinil ("S-MDF") as measured by HPLC, where the lower limit is the limit of detection (QL) for the HPLC apparatus. The amounts of R-MDF-DS and S-MDF present in armodafinil are determined by the HPLC methods as described in the example section below.

In one embodiment, the present invention encompasses a process for purifying armodafinil from R-MDF-DS comprising: dissolving crude armodafinil in ethanol to form a solution; adding a solvent selected from the group consisting of linear or branched $C_5$-$C_8$ alkyl, linear or branched $C_5$-$C_8$ ether, and mixtures to the solution to form a reaction mixture; cooling the reaction mixture; and isolating purified armodafinil from the reaction mixture.

Crude armodafinil may be prepared according to U.S. Pat. No. 4,927,855, hereby incorporated by reference.

The dissolving step, in the purification process, is typically performed while heating. Preferably, the solution is heated at a temperature of about 50° C. to about reflux temperature. As used herein, unless otherwise defined, the term "reflux temperature" refers to a temperature of about 70° C. to 80° C. at atmospheric pressure, and preferably, about 75° C. to 78.5° C. at atmospheric pressure. More preferably, the solution is heated at a temperature of about 50° C. to about 60° C., and most preferably, it is heated at a temperature of about 50° C. to about 55° C. As used herein, unless otherwise defined, the term "atmospheric pressure" refers to standard pressure at 1 Atm or 760 mm Hg (torr).

Preferably, the ethanol used is absolute ethanol. Preferably, the amount of ethanol present is at about 10 ml to about 30 ml per gram of crude armodafinil, and more preferably about 10 ml to about 25 per gram of crude armodafinil. Typically, when the solution is heated at a temperature of about 50° C. to about 55° C., about 25 to 30 ml of ethanol per gram of crude armodafinil is added, and when the solution is heated at about reflux temperature, about 10 ml of ethanol per gram of crude armodafinil is added.

Optionally, after the dissolving step and prior to the solvent addition, the solution is treated with activated alumina, preferably either by mixing it with activated alumina or by circulating it through a bed of activated alumina, followed by removal of the alumina. Preferably, the activated alumina is basic. For example, the activated alumina is added to the solution containing ethanol and crude armodafinil. Preferably, the activated alumina is present in about 10-30% by weight to the crude armodafinil, more preferably in about 10-20% or 15-25% by weight, and most preferably in about 20% by weight. After the activated alumina addition, a slurry is obtained. Preferably, the slurry is stirred for about 30 minutes to about 24 hours, and more preferably, the slurry is stirred for about 30 minutes to about 2 hours. Typically, the activated alumina is removed by filtration. After the removal of the activated alumina, a solution and a wet filter cake of the activated alumina are obtained separately. Typically, the wet filter cake of the activated alumina is washed with ethanol. Preferably, it is washed with absolute ethanol.

When the solution is circulated through a bed of activated alumina, typically, the circulation time is depended on the size of the circulation column. Preferably, the solution is circulated through a bed of activated alumina for about 30 minutes to about 24 hours. More preferably, it is circulated for about 30 minutes to about 4 hours. After the circulation is complete, the activated alumina is removed by filtration. Optionally, a filter aid such as "Hyflo™" is used to improve filtration and circulation rate. Preferably, the filter aid is present in about 5% to 20% by weight and more preferably in about 10% by weight to the crude armodafinil.

Optionally, the dissolving step of the purification further comprises reduction of the volume of ethanol prior to adding the solvent. If an activated alumina treatment is applied, the volume reduction will take place after mixture with the activated alumina. Typically, the amount of ethanol is reduced to about 25 ml to about 9 ml, preferably, it is reduced to about 15 ml to about 9 ml, and most preferably to about 11 ml to about 10 ml per gram of crude armodafinil. The reduction of ethanol may be carried out by evaporation under reduced pressure, preferably by vacuum distillation. Preferably, the evaporation is carried out at a temperature of not more than about 30° C. During evaporation, a slurry is obtained. The slurry may be heated at a temperature of about 50° C. to about reflux temperature. More preferably, the slurry is heated at a temperature of about 50° C. to about 60° C. Most preferably, it is heated to a temperature of about 50° C. to about 55° C.

Typically, the solvent is selected from the group consisting of linear or branched $C_5$-$C_8$ alkyl, linear or branched $C_5$-$C_8$ ether, and mixtures thereof. Preferably, the linear or branched $C_5$-$C_8$ alkyl is n-hexane, n-heptane, or n-octane. Preferably, the linear or branched $C_5$-$C_8$ ether is methyl tert-butyl ether ("MTBE"), or alkoxy ethers such as dimethoxyethane or diethoxyethane ("DEM"). More preferably, the solvent is n-heptane, n-hexane, methyl tert-butyl ether, diethoxyethane or mixtures thereof.

Preferably, the amount of solvent present is at about 6 to about 9 ml to per gram of crude armodafinil.

After the addition of the solvent, a reaction mixture is obtained. The reaction mixture may be a slurry or a solution. Typically, the reaction mixture is stirred for about 30 minutes to about 3 hours after the addition of the solvent. During the dissolving step, when the activated alumina is mixed with the solution and is being heated at about reflux temperature, the stirring is preferably less than about 3 hours, more preferably for about one to three hours, and most preferably from about 2 to about 2.5 hours.

Subsequently, the reaction mixture is cooled. Typically, the cooling step is carried out for an amount of time sufficient to induce crystallization of armodafinil. Preferably, the cooling step is done at a temperature of about 5° C. to about −20° C. More preferably, the cooling step is done at a temperature of about 0° C. to about −15° C. Optionally, when the reaction mixture is a solution, it may be seeded with crystals of pure armodafinil during the cooling step. Preferably, after seeding, a slurry is obtained and the slurry is stirred. Typically, the reaction mixture is cooled for a sufficient amount of time to obtain the crystalline pure armodafinil. Preferably, the reaction mixture is cooled for about 5 hours to about 12 hours.

The process further comprises an isolating step. Isolation of pure armodafinil can be achieved using any methods known in the art, for example, by vacuum filtration.

The product obtained is typically pure armodafinil. The pure armodafinil product obtained as a result of the process preferably contains less than the quantization limit ("QL") of about 0.05% area of R-MDF-DS, as measured by HPLC.

Preferably, the product also contains less than about 0.05% area of S-modafinil as measured by HPLC.

The present invention also encompasses a process for preventing the transformation of armodafinil to S-modafinil during its dissolution, while treating it with activated $Al_2O_3$. Applicants have found that transformation of armodafinil to S-modafinil can be prevented by increasing the amount of ethanol used in the process. When the volume of ethanol is increased, the dissolution temperature decreases, which prevents the transformation of armodafinil to S-modafinil. Therefore, the amount of ethanol present in the above process has to be at least 15 ml of ethanol per gram of crude armodafinil. In addition, the activated $Al_2O_3$ is used to reduce the amount of modafinic acid ("BHSO") in armodafinil, for example, by contacting a solution of armodafinil with activated alumina.

This embodiment of the invention encompasses a process for preventing the transformation of armodafinil to S-modafinil comprising: dissolving crude armodafinil in at least about 15 ml of ethanol per gram of crude armodafinil to form a solution; adding or circulating activated basic or neutral $Al_2O_3$ to the solution to form a reaction mixture; and isolating the armodafinil from the reaction mixture. As used herein, the term "transformation of armodafinil to S-modafinil" refers to the potential transformation of armodafinil to S-modafinil during the treatment with activated alumina.

Preferably, the ethanol is absolute ethanol. Preferably, the activated $Al_2O_3$ is present is present in about 20% by weight to crude armodafinil.

After the activated alumina addition, a slurry is obtained. Preferably, the slurry is stirred for about 30 minutes to about 24 hours, and more preferably, the slurry is stirred for about 30 minutes to about 2 hours. Typically, the activated alumina is removed by filtration. After the removal of the activated alumina, a solution and a wet filter cake of the activated alumina are obtained separately. Typically, the wet filter cake of the activated alumina is washed with ethanol. Preferably, it is washed with absolute ethanol.

When the solution is circulated through a bed of activated alumina, typically, the circulation time is depended on the size of the circulation column. Preferably, the solution is circulated through a bed of activated alumina for about 30 minutes to about 24 hours. More preferably, it is circulated for about 30 minutes to about 4 hours. After the circulation is complete, the activated alumina is removed by filtration. Optionally, a filter aid such as "Hyflo™" is used to improve filtration and circulation rate. Preferably, the filter aid is present in about 5% to 20% by weight and more preferably in about 10% by weight to the crude armodafinil.

The dissolving step, in the prevention process, is typically performed while heating. Preferably, the solution is heated at a temperature of about 50° C. to about reflux temperature. As used herein, unless otherwise defined, the term "reflux temperature" when referring to the prevention process refers to a temperature of about 70° C. to 80° C. at atmospheric pressure, and preferably, about 75° C. to 78.5° C. at atmospheric pressure. More preferably, the solution is heated at a temperature of about 50° C. to about 60° C., and most preferably, it is heated at a temperature of about 50° C. to about 55° C. As used herein, unless otherwise defined, the term "atmospheric pressure" refers to standard pressure at 1 Atm or 760 mm Hg (torr).

Optionally, the dissolving step of the purification further comprises reduction of the volume of ethanol prior to adding the solvent. If an activated alumina treatment is applied, the volume reduction will take place after mixture with the activated alumina. Typically, the amount of ethanol is reduced to about 25 ml to about 9 ml, preferably, it is reduced to about 15 ml to about 9 ml, and most preferably to about 11 ml to about 10 ml per gram of crude armodafinil. The reduction of ethanol may be carried out by evaporation under reduced pressure, preferably by vacuum distillation. Preferably, the evaporation is carried out at a temperature of not more than about 30° C. During evaporation, a slurry is obtained. The slurry may be heated at a temperature of about 50° C. to about reflux temperature. More preferably, the slurry is heated at a temperature of about 50° C. to about 60° C. Most preferably, it is heated to a temperature of about 50° C. to about 55° C.

Optionally, prior to the isolation step, a solvent may be added. The solvent is selected from the group consisting of linear or branched $C_5$-$C_8$ alkyl and linear or branched $C_5$-$C_8$ ether. Preferably, the linear or branched $C_5$-$C_8$ alkyl is n-hexane, n-heptane, or n-octane. Preferably, the linear or branched $C_4$-$C_8$ ether is methyl tert-butyl ether, dimethoxyethane or diethoxyethane. More preferably, the solvent is n-heptane, methyl tert-butyl ether, n-hexane, diethoxyethane, or mixtures thereof.

Preferably, the amount of solvent present is at about 6 to about 9 ml to per gram of crude armodafinil.

After the addition of the solvent, a reaction mixture is obtained. The reaction mixture may be a slurry or a solution. Typically, the reaction mixture is stirred for about 30 minutes to about 3 hours after the addition of the solvent. During the dissolving step, when the activated alumina is mixed with the solution and is being heated at about reflux temperature, the stirring is preferably less than about 3 hours, more preferably for about one to three hours, and most preferably from about 2 to about 2.5 hours.

The process further comprises isolating the product. However, prior to the isolation step, a cooling step may be performed. Typically, the cooling step is carried out for an amount of time sufficient to induce crystallization of armodafinil. Preferably, the cooling step is done at a temperature of about 5° C. to about −20° C. More preferably, the cooling step is done at a temperature of about 0° C. to about −15° C. Optionally, when the reaction mixture is a solution, it may be seeded with crystals of pure armodafinil during the cooling step. Preferably, after seeding, a slurry is obtained and the slurry is stirred. Typically, the reaction mixture is cooled for a sufficient amount of time to obtain the crystalline pure armodafinil. Preferably, the reaction mixture is cooled for about 5 hours to about 12 hours.

The isolation can be achieved using any method known in the art, for example, by filtration, washing and drying. Preferably, the washing is with absolute ethanol. Preferably, the drying is under vacuum at a temperature of about 40° C. to about 80° C.

Preferably, the product obtained from the above process for preventing transformation of armodafinil to S-modafinil also contains less than about 0.05% area of S-MDF, as measured by HPLC.

Having described the invention with reference to certain preferred embodiments, other embodiments will become apparent to one skilled in the art from consideration of the specification. The invention is further defined by reference to the following examples describing in detail the purification of armodafinil. It will be apparent to those skilled in the art that many modifications, both to materials and methods, may be practiced without departing from the scope of the invention.

EXAMPLES

HPLC Methods

I. Determination of Optical Purity of Armodafinil by HPLC

The optical purity of armodafinil was determined by high performance liquid chromatography under the following conditions. A Chiralpak® AD-H column was used with 4.6*150 mm DAIC 19324 packing. The eluent was a mixture of 80% heptane, 20% ethanol and 0.1% trifluoroacetic acid. The flow-rate was 1.5 ml/min, the UV detector was set at 225 nm and the column temperature was 25° C. The sample volume was 20 µL and the diluent was ethanol.

System suitability tests were performed before samples were analyzed. The system suitability solution was prepared as follows: accurately weighed about 10 mg of (±) modafinil standard in a 20 ml volumetric flask, dissolved and diluted it with diluent using sonicator. The system suitability solution was injected into the column under the above-described conditions. Typical retention times for R-MDF was ~8.2 minutes, and ~11.1 minutes for S-MDF. A resolution factor between the R-MDF and S-MDF peak not less than 1.8 was achieved. The purity of armodafinil was determined and calculated as % area.

Each sample solution was prepared as follows: accurately weighed about 10 mg of R-modafinil ("R-MDF") sample in a 20 ml volumetric flask, dissolved and diluted it with diluent using sonicator.

II. Impurity Profile Determination of Armodafinil

The % impurity of armodafinil was determined by high performance liquid chromatography under the following conditions. A YMC basic 100 mm×3.0 BA 99S031003QT column was used. The flow-rate was 0.6 ml/min, the UV detector was set at 225 nm and the column temperature was 25° C. The sample volume was 10 µL. The diluent was a mixture of water and acetonitrile (50:50). The results were calculated as % area.

Samples were eluted from the column by gradient elution with eluents A and B. The equilibration time was 5 minutes. Eluent A was a mixture of 72% buffer and 28% acetonitrile. Eluent B was a mixture of 30% buffer and 60% acetonitrile: isopropyl:alcohol (1:10). The buffer was 0.02M $KH_2PO_4$ (adjusted to pH of 4.0 with $H_3PO_4$). The auto sampler temperature was 25° C. At time=0 minute, 100% eluent A was used. At time=8 minutes, the eluent was a mixture of 70% eluent A and 30% eluent B. At t=20 minutes, the eluent was a mixture of 10% eluent A and 90% eluent B.

Mobile phase composition and flow rate may be varied in order to achieve the required system suitability.

The sample solution was prepared as follows: accurately weighed about 20 mg of R-MDF sample in a 50 ml volumetric flask and dissolved it in 25 ml of acetonitrile and diluted to volume with water, and then 5 ml of this sample solution was obtained and diluted it further with 20 ml water.

The system suitability test was performed by injecting into the column with a system suitability solution and a sample solution, the sample solution ran through the chromatograph continuously up to 30 minutes. The areas for each peak were determined in each solution using a suitable integrator.

% impurity in armodafinil was calculated as follows:

$$\% \text{ impurity} = \frac{\text{area impurity in sample}}{\text{Total area}} \times 100$$

Example 1

Purification by Crystallization of Crude Armodafinil from Absolute Ethanol/N-Heptane Mixture Crude armodafinil (21 g) and absolute ethanol (210 ml) were charged into a 1 liter stirred glass lab reactor. The stirrer was turned on and the reaction mixture was heated to reflux (78° C.). After the armodafinil was dissolved, 2.1 g of activated basic alumina was added, and the reaction mixture was stirred with the activated basic alumina for 30 minutes at 78° C. The activated basic alumina was removed from the reaction mixture by pressure filtration; afterwards the reaction mixture was washed with absolute ethanol. The clear reaction mixture was charged back, and heated to reflux (78° C.). At 78° C., 126 ml of n-heptane was added, which causes the reflux temperature to decrease to 72.2° C. The reaction mixture was cooled to 64.8° C., and then seeded with milled crystals of armodafinil. The seeded reaction mixture was stirred at 64.8-65° C. for 15 minutes, and then cooled to 0° C. during 5 hr. The obtained seeded reaction mixture was stirred at 0° C. for additional 13.5 hr, and then the product was isolated by vacuum filtration. The filter cake was washed with 21 ml of absolute ethanol, and then the wet product was dried under reduced pressure in a lab oven heated to 60° C. 17 g of armodafinil crystals was obtained (81% yield w/w).

The purity of the product was determined by HPLC, and the impurity R-MDF-DS was not detected or found within the limits of detection. The concentration of the R-MDF-DS in the starting R-MDF crude was: 1.08% (crude purity: 97.7%, crystal purity: 99.9% area as measured by HPLC)

Example 2

Purification by Crystallization of Crude Armodafinil from Absolute Ethanol/MTBE Mixture A reaction mixture (350 g) containing 40 g of crude armodafinil in absolute ethanol (10 ml/g of crude armodafinil), after treatment with activated basic alumina (using the conditions of Example 1) were charged into a 1 liter stirred glass lab reactor. The stirrer was turned on and the reaction mixture was heated to reflux (78.5° C.). Then 240 ml of MTBE was added, which causes the reflux temperature to decrease to 65.8° C. Then the reaction mixture was cooled to 61° C. At 61° C. the reaction mixture was seeded with milled crystals of armodafinil. The seeded reaction mixture was stirred at 60.8-61° C. for 10 minutes, and then cooled to 0° C. during 5 hr. The obtained seeded reaction mixture was stirred at 0.1° C. for additional 13 hr, and the product was isolated by vacuum filtration. The filter cake was washed with 40 ml of absolute ethanol, and then the wet product was dried under reduced pressure in a lab oven heated to 60° C. 32.1 g of armodafinil crystals was obtained (80.2% yield w/w).

The purity of the product was determined by HPLC, and the impurity R-MDF-DS was not detected or found within the limits of detection. The concentration of the R-MDF-DS in the starting R-MDF-crude was: 1.16% (crude purity: 96.9%, crystal purity: 99.8% area as measured by HPLC).

Example 3

Purification by Crystallization of Crude Armodafinil from Absolute Ethanol/Diethoxymethane (DEM) Mixture A reaction mixture (350 g) containing 40 g of crude armodafinil in absolute ethanol (10 ml of ethanol per gram of crude armodafinil), after treatment with alumina were charged in to a 1 liter stirred glass lab reactor (using the conditions of Example 1). The stirrer was turned on and the reaction mixture was heated to reflux (78.5° C.). Then 240 ml of diethoxymethane was added, which causes the reflux temperature to decrease to 76° C. Then the reaction mixture was cooled to 55° C. At 55° C. the reaction mixture was seeded with milled crystals of armodafinil. The seeded reaction mixture was stirred at 54-55° C. for 30 min, and then cooled to 0° C. during 5 hr. The obtained seeded reaction mixture was stirred at 0.1° C. for additional 12 hr, and then the product was isolated by vacuum filtration. The filter cake was washed with 40 ml of absolute ethanol, and then the wet product was dried under reduced pressure in a lab oven heated to 60° C. 31 g of armodafinil crystals was obtained (77.5% yield w/w).

The purity of the product was determined by HPLC, and the impurity R-MDF-DS was not detected or found within the limits of detection. The concentration of the R-MDF-DS in the starting RMDF crude was: 1.16%.
(crude purity: 96.9%, crystal purity: 99.9% area as measured by HPLC)

Example 4

Treatment in 20 Volumes of Absolute Ethanol, and Crystallization of Crude Armodafinil from Absolute Ethanol/MTBE Mixture Crude armodafinil (40 g) and 800 ml absolute ethanol were charged into a 1 liter stirred glass lab reactor. The stirrer was turned on and the solution was heated to 58.4° C. At 58.4° C., the product was completely dissolved. The optical purity of the solution was tested, and then 8 g of activated basic alumina were charged. The solution was treated with activated basic alumina, and sampled after 1, 4, 5 hrs for optical purity determination. The solution was cooled to 0° C., and kept over-night. Then the solution was heated again to 58° C., and the used Alumina was separated by vacuum filtration. After cleaning the reactor with fresh absolute ethanol, the filtered solution was charged back. The solvent was evaporated at reduced pressure, and at a reactor temperature of: 42-63° C. (jacket temperature of 60-65° C.). When the volume of the solution in the reactor has been reduced to the ratio of: 10 volumes vs. crude armodafinil, the evaporation was stopped by increasing pressure to ambient with nitrogen. During the evaporation, since the volume of the solvent and the reactor temperature has been reduced, the product precipitated. The slurry was heated to reflux (78° C.), and after obtaining dissolution, 120 ml of MTBE were charged, which caused the reflux temperature to decrease to 72° C. Then the solution was cooled to 50° C. At 50° C. the solution was seeded with milled crystals of armodafinil. The seeded solution was stirred at 50° C. for 30 minutes, and then cooled to 0° C. during 5 hr. The obtained slurry was stirred at 0° C. for over-night.

The product was isolated by vacuum filtration. The filter cake was washed with 40 ml of absolute ethanol, and then the wet product was dried under reduced pressure in a lab oven heated to 60° C. 30.2 g of dry armodafinil crystals was obtained (75.5% yield).

The optical purity of the product was determined by HPLC, and the concentration of the S-isomer in the sample is presented in Table No. 3, Sample 2.

Example 5

Treatment in 25 Volumes of Absolute Ethanol, and Crystallization of Crude Armodafinil from Absolute Ethanol/MTBE Mixture Crude armodafinil (40 g) and 1000 ml absolute ethanol were charged in to a 1 liter stirred glass lab reactor. The stirrer was turned on and the solution was heated to 53.2° C. At 53.2° C. the product was completely dissolved, and then 8 g of activated basic alumina were charged (using the conditions of Example 1). The solution was treated with activated basic alumina for 6 hrs and then the used alumina was separated by vacuum filtration. The separated alumina was washed with one volume of ethanol. Then the solution was cooled to 10° C., and kept over-night. Then the solution was heated again to 53° C. The solvent was evaporated at reduced pressure, and at a jacket temperature of 55-65° C. When the volume of the solution in the reactor has been reduced to the ratio of: 10 volumes vs. crude armodafinil, the evaporation was stopped by increasing the pressure to ambient with nitrogen. During the evaporation, since the volume of the solvent and the reactor temperature has been reduced, the product precipitated. The slurry was heated to reflux (76° C.), and after obtaining dissolution, 120 ml of MTBE was charged, which caused the reflux temperature to decrease to 72° C. Then the solution was cooled to 50° C. At 50° C., the solution was seeded with milled crystals of armodafinil. The seeded solution was stirred at 50° C. for 10 minutes, and then cooled to 0° C. during 1.5 hr. The obtained slurry was stirred at 0° C. for over-night. The product was isolated by vacuum filtration. The filter cake was washed with 40 ml of absolute ethanol, and then the wet product was dried under reduced pressure in a lab oven heated to 60° C. 31 g of dry armodafinil crystal was obtained (77.5% yield).

The purity of the product was determined by HPLC, and the concentration of the S-isomer is presented in Table No. 3, Sample 4.

Example 6

Purification by Crystallization of Crude Armodafinil from Ethanol/MTBE Mixture without Obtaining Complete Dissolution Before Cooling Crude armodafinil (40 g) and 1000 ml absolute ethanol (25 vol) were charged in to a 1 liter stirred glass lab reactor. The stirrer was turned on and the solution was heated to 52° C. At 52° C. the product was completely dissolved. The optical purity of the solution was tested, and then 8 g of activated basic alumina were charged. The solution was treated with activated basic alumina, and sampled after 1, 2.5, 5.5 hrs for optical purity determination. The used alumina was separated by vacuum filtration, washed with one volume of ethanol, and then the solution was cooled to 110° C., and kept over-night. Then the solution was heated again to 53° C. and sampled for optical purity determination. The solvent was evaporated at reduced pressure, and at a jacket temperature of 55-65° C. When the volume of the solution in the reactor has been reduced to the ratio of: 10 volumes vs. crude armodafinil (10 ml/g), the evaporation was stopped by increasing pressure to ambient with nitrogen. During the evaporation, since the volume of the solvent and the reactor temperature has been reduced, the product precipitated. Then, 120 ml of MTBE were charged, at a jacket temperature of 55° C. Then the solution was cooled to 0° C. during 2 hr. The obtained slurry was stirred at 0° C. for overnight.

The product was isolated by vacuum filtration. The filter cake was washed with 40 ml of absolute ethanol, and then the wet product was dried under reduced pressure in a lab oven heated to 60° C. 30 g of dry armodafinil crystal was obtained (75% yield).

The purity of the product was determined by HPLC, and the concentration of the S-isomer in the sample is presented in Table No. 3, sample 3.

Example 7

Purification by Crystallization of Crude Armodafinil from Absolute Ethanol/MTBE Mixture without Dissolution and Seeding Dry crude armodafinil (40 g) and 1000 ml of absolute ethanol (25 vol) were charged into a 1 liter glass stirred reactor. The mixer was turned on and the mixture was heated to a temperature of 55° C. to dissolve the armodafinil. 8 g of activated basic alumina were charged, and the mixture was stirred for 1 hr. Afterwards, 4 g of "Hyflo™" were charged, and then the solution was vacuum filtered. The concentration of BHSO in the clear solution was tested and found to be: 0.05%. The filtrate was charged back in to the reactor, and the solvent was evaporated to 10 vol under reduced pressure, and at a maximum jacket temperature of 55° C. After completion of the evaporation, the reactor pressure was increased to ambient, and the slurry was heated to a temperature of 55° C. Then, 240 ml of MTBE was charged, and the reactor was stirred for 30 minutes at a temperature of 55° C. Afterwards, the slurry was cooled to a temperature of 0° C. during 5 hrs. The slurry was stirred at that temperature for overnight, and then the product was isolated by vacuum filtration, and the wet filter cake was washed with 40 ml of absolute ethanol (1 vol). The wet product was dried in a tray oven at reduced pressure and at a temperature of 60° C. 28.5 g of armodafinil crystal was obtained (71.2% w/w). The product was tested, and it was found that the concentration of S-MDF is: 0.02% (in the R-MDF-crude the concentration of S-MDF: 0.06%). In addition, it was found that the impurity R-MDF-DS is not present (the concentration in R-MDF-crude: 1.74%). Modafinic acid was present in <0.05%.

Example 8

Purification by Crystallization of Armodafinil from Absolute Ethanol/MTBE Mixture—Industrial Scale Dry crude armodafinil (28.8 kg) and absolute ethanol (597.7 kg) were charged into a 1 m3 glass lined stirred reactor. The mixer was turned on and the mixture was heated to a temperature of 55.5° C. to dissolve the armodafinil. The solution was circulated through a bed consisting of 5.8 kg activated basic alumina and 2.9 kg of "Hyflo™" (the bed was prepared separately at beginning of production of the batch).

After 6 hrs of circulation, the concentration of BHSO was tested and found to be 0.17%, after additional 2 hrs of circulation (total: 8 hrs of circulation), the solution was tested again and it was found that there is no BHSO in the solution (complete removal). Then the solution was filtered through the bed and through polishing filters into a second 1 m3 glass lined stirred reactor. Then the bed of Alumina/Hyflo™ was washed with 56.9 Kg of absolute ethanol (2.5 L/kg of crude armodafinil), and the filtrate was collected into the second glass lined reactor. The stirrer in the second reactor was turned on, and the solution was cooled to 9.8° C., and then the pressure in the reactor was reduced to 54 mm Hg. The reactor jacket was heated gradually to 44.1° C. to obtain reflux. When reflux has been obtained the system was turned to distillation mode, and the distillate was collected. During the evaporation, 412 kg of ethanol were removed from the reactor at a pressure of 54-57 mm Hg, at a maximum jacket temperature of 50.9° C., and at a maximum reactor temperature of 26.2° C. The volume of solvent left in the reactor: 10.7 liter per kg of crude armodafinil. After completion of the evaporation, the reactor pressure has been increased to ambient, and the slurry was heated to a temperature of 53.2° C. Then, 191.8 kg of MTBE (9 vol) were charged, and the reactor was stirred for 2 hrs at a temperature of 57° C. Afterwards, the slurry was cooled to a temperature of −6.2° C. during 6 hrs. The slurry was stirred at that temperature for 2 hrs, and then the product was isolated by pressure filtration in a filter drier, and the wet filter cake was washed with 22.8 kg of absolute ethanol (1 vol). The washed filter cake was dewatered by mechanically squeezing, and then stirred dried at a pressure of 46-62 mm Hg, and at a jacket temperature of 60° C. The drying continued until the loss on drying of the product was: 0.04% (tested by moisture analyzer at 90° C.). 21.4 kg of armodafinil crystal was obtained (74.3% w/w).

The product was tested, and it was found that the concentration of S-MDF is: 0.03% (in the R-MDF-crude the concentration of S-MDF: 0.05%). In addition, it was found that the impurity R-MDF-DS is not present (the concentration in RMDF-crude: 1.23%).

Analytical Results

Table No. 1 presents results of monitoring of S-isomer during 45 minute treatment with alumina in 10 volumes of absolute ethanol at 78° C. (reflux). The purification was carried out in absolute ethanol only.

TABLE NO. 1

The effect of short term alumina treatment of armodafinil in 10 volumes solution of absolute ethanol at 78° C.

| Sample | Description | % [% area] S-MDF in armodafinil |
|---|---|---|
| 1 | Crude armodafinil | 0.04 |
| 2 | Dissolved crude | 0.10 |
| 3 | Treated solution for 45 min | 0.27 |
| 4 | Solid precipitated at 30° C. | 0.08 |
| 5 | Mother liquor at 30° C. | 0.62 |
| 6 | Solid precipitated at 15° C. | 0.06 |
| 7 | Mother liquor at 15° C. | 0.86 |
| 8 | Solid precipitated at 0° C. (t = 0) | 0.09 |
| 9 | Mother liquor at 0° C. | 1.33 |
| 10 | Solid precipitated at 0° C. (during cooling, before washing) | 0.07 |
| 11 | Mother liquor at 0° C. | 1.45 |
| 12 | Solid precipitated at 0° C. (t = 12-16 hrs) (after washing) | 0.09 |
| 13 | Mother liquor at 0° C. | 0.32 |
| 14 | Armodafinil crystal dry | 0.08 |

It can be concluded based on the results presented in Table No. 1 that during the short term treatment (e.g. 45 minutes) with activated basic alumina, there is partial transformation from amodafinil to S-modafinil. However, the products isolated during the cooling step and at the isolating step are essentially free of S-modafinil.

Table No. 2 presents results of monitoring of S-isomer during prolonged term treatment with alumina in 10 volumes solution of absolute ethanol at 78° C.

TABLE NO. 2

The effect of prolonged term (22 hours) alumina treatment of armodafinil in 10 volumes of absolute ethanol

| Sample | Description | % S-MODAFINIL |
|---|---|---|
| 1 | Crude armodafinil | 0.06 |
| 2 | Solution before treatment with Alumina t = 0 | 0.171 |
| 3 | 1 hr Alumina treatment | 0.570 |
| 4 | 4 hr Alumina treatment | 1.143 |
| 5 | 6 hr Alumina treatment | 1.500 |
| 6 | 22 hr Alumina treatment | 5.092 |
| 7 | Dry product | 2.943 |

It can be concluded based on the results presented in Table No. 2 that if the treatment with alumina lasts for a long period of time (e.g. 1 to 22 hours), then the concentration of S-modafinil increases to a level at which it will not be easily removed by crystallization.

TABLE NO. 3

The effect of prolonged term alumina treatment of armodafinil in 15-25 volumes of absolute ethanol

| EXPERIMENT | Example 1 | Example 2 | Example 3 (*) | Example 4 (*) |
|---|---|---|---|---|
| Volume | 15 | 20 | 25 | 25 |
| S-MDF content of crude armodafinil [% area] | 0.06 | 0.06 | NT | NT |
| Dissolution temperature [° C.] | 63.4 | 58.4 | 52 | 52 |
| S-MDF content of solution before treatment [% area] | 0.084 | 0.060 | 0.048 | NT |
| S-MDF content in 1$^{st}$ sample after 1 hr of treatment [% area] | 0.110 (1) | 0.078 (1) | 0.049 (1) | NT |

TABLE NO. 3-continued

The effect of prolonged term alumina treatment of armodafinil in 15-25 volumes of absolute ethanol

| EXPERIMENT | Example 1 | Example 2 | Example 3 (*) | Example 4 (*) |
|---|---|---|---|---|
| S-MDF content in $2^{nd}$ sample after 2.5 to 4 hrs of treatment [% area] | 0144 (4) | 0.101 (4) | 0.076 (2.5) | NT |
| S-MDF content in $3^{rd}$ sample after 5 to 5.5 hrs of treatment [% area] | 0.184 (5) | 0.101 (5) | 0.067 (5.5) | NT |
| S-MDF content in armodafinil crystal [% area] | 0.065 | 0.030 | 0.02 | 0.01 |
| Solvent mixture EtOH/MTBE [vol] | 10/3 | 10/3 | 10/3 (*) | 10/3 (*) |
| Yield [%] (not including samples) | 75.5 | 79.5 | 75 | 77.5 |

NT = Not Tested, when necessary time is provided in parenthesis.
(*) In Experiment 3, there was no complete dissolution before the crystallization, and in Experiment 4, the crystallization was from solution.

It can be further concluded based on the results presented in Table No. 3 that as the amount of ethanol increases, the dissolution temperature decreases, which lowers the concentration of S-modafinil and as a result, prevents the transformation of armodafinil to S-modafinil.

We claim:

1. A process for purifying armodafinil from bis(diphenylmethyl)disulfide comprising:
dissolving crude armodafinil in ethanol to form a solution; adding a solvent selected from the group consisting of linear or branched $C_5$-$C_8$ alkane, linear or branched $C_5$-$C_8$-ether, and mixtures thereof to the solution to form a reaction mixture; cooling the reaction mixture; and isolating pure armodafinil from the reaction mixture.

2. The process according to claim 1, wherein the ethanol is absolute ethanol.

3. The process according to claim 1, wherein the linear or branched $C_5$-$C_8$ alkane or the linear or branched $C_5$-$C_8$ ether is n-heptane, n-hexane, n-octane, methyl tert-butyl ether, diethoxyethane, or dimethoxyethane.

4. The process according to claim 1, wherein the amount of ethanol present is at about 10 ml to about 30 ml of ethanol per gram of crude armodafinil.

5. The process according to claim 1, wherein the amount of the solvent present is about 6 to about 9 ml per gram of crude armodafinil.

6. The process according to claim 1, wherein the dissolving step is performed while heating.

7. The process according to claim 6, wherein the solution is heated at a temperature of about 50° C. to about reflux temperature.

8. The process according to claim 1, further comprising treating the solution with activated alumina prior to adding a solvent; and removing the alumina by filtration prior to adding the solvent.

9. The process according to claim 8, wherein the activated alumina is present in about 10% to about 30% by weight to the crude armodafinil.

10. The process according to claim 1, wherein the dissolving step further comprises reducing the amount of ethanol prior to adding the solvent.

11. The process according to claim 10, wherein the ethanol is reduced in an amount of about 9 volumes to about 25 ml per gram of crude armodafinil.

12. The process according to claim 1, wherein the cooling step is performed at a temperature of about 5° C. to about −20° C.

13. The process according to claim 1, wherein the pure armodafinil contains less than about 0.05% area of bis(diphenylmethyl)disulfide, as measured by HPLC.

14. The process according to claim 1, wherein the pure armodafinil contains less than about 0.05% area of S-modafinil, as measured by HPLC.

15. A process for preventing the transformation of armodafinil to S-modafinil comprising: dissolving crude armodafinil in at least about 15 ml of ethanol per gram of crude armodafinil to form a solution; adding activated basic or neutral $Al_2O_3$ to the solution to form a reaction mixture; and isolating the purified armodafinil from the reaction mixture.

16. The process according to claim 15, wherein the ethanol is absolute ethanol.

17. The process according to claim 15, wherein the activated basic or neutral $Al_2O_3$ is present in an amount of about 20% by weight of the crude armodafinil.

18. The process according to claim 15 further comprising adding a solvent prior to the isolation step.

19. The process according to claim 18, wherein the solvent is selected from the group consisting of linear or branched $C_5$-$C_8$ alkane, linear or branched $C_5$-$C_8$ ether, and mixtures thereof.

20. The process according to claim 15, wherein the linear or branched $C_5$-$C_8$ alkane or the linear or branched $C_5$-$C_8$ ether is n-heptane, n-hexane, n-octane, methyl tert-butyl ether, diethoxyethane, or dimethoxyethane.

21. The process according to claim 15, wherein the amount of the solvent present is at about 6 to about 9 volumes of the crude armodafinil.

22. The process according to claim 15 further comprising cooling the reaction mixture prior to the isolating the purified armodafinil.

23. The process according to claim 15, wherein the purified armodafinil contains less than about 0.05% area of S-modafinil, as measured by HPLC.

* * * * *